US006176869B1

United States Patent
Mason et al.

(10) Patent No.: US 6,176,869 B1
(45) Date of Patent: Jan. 23, 2001

(54) FLUID DRIVE MECHANISM FOR A THERAPEUTIC TREATMENT SYSTEM

(75) Inventors: Jeffrey T. Mason, Escondido; Richard W. Royer, Fallbrook, both of CA (US)

(73) Assignee: Breg, Inc., Vista, CA (US)

( * ) Notice: Under 35 U.S.C. 154(b), the term of this patent shall be extended for 0 days.

(21) Appl. No.: 09/257,796

(22) Filed: Feb. 25, 1999

(51) Int. Cl.$^7$ ........................................ A61F 7/00
(52) U.S. Cl. .......................... 607/104; 607/114; 601/15
(58) Field of Search ................... 607/104, 108, 607/114; 601/15, 17; 165/46

(56) References Cited

U.S. PATENT DOCUMENTS

| | | | |
|---|---|---|---|
| 4,184,537 | * 1/1980 | Sauder | 165/46 |
| 4,459,468 | * 7/1984 | Bailey | 219/490 |
| 4,756,310 | * 7/1988 | Bitterly | 128/400 |
| 4,962,761 | * 10/1990 | Golden | 128/400 |
| 5,080,089 | * 1/1992 | Mason et al. | 128/24 |
| 5,241,951 | * 9/1993 | Mason et al. | 607/104 |
| 5,476,489 | * 12/1995 | Koewler | 607/104 |
| 5,806,335 | * 9/1998 | Herbert et al. | 62/434 |
| 5,888,185 | * 3/1999 | Regan | 600/15 |
| 5,980,561 | * 11/1999 | Kolen et al. | 607/104 |

OTHER PUBLICATIONS

Cryo/Cuff and AutoChill System commercially available Feb. 1994 as disclosed in "Cryo/Cuff Compression Dressings" Product Brochure.

Wilden Pump commercially available Dec. 1955 as disclosed in "The Wilden Pump–How It works" Product Specification Sheet.

* cited by examiner

Primary Examiner—Michael Peffley
Assistant Examiner—Jocelyn Ram
(74) Attorney, Agent, or Firm—Rodney F. Brown

(57) ABSTRACT

A system for therapeutically treating a desired region of a patient's body by circulating a nonambient temperature treatment fluid through a pad positioned on the treatment region. The system is provided with a fluid drive mechanism including a flow control assembly and a pump for delivering a drive fluid to the flow control assembly. The flow control assembly houses a pressurizing chamber having a drive fluid inlet and outlet and a treatment fluid inlet and outlet. A drive fluid outlet valve and treatment fluid inlet valve are provided to selectively restrict flow through the drive fluid outlet and treatment fluid inlet, respectively. Operation of the flow control assembly initiates with both the drive fluid outlet valve and treatment fluid inlet valve in an open position, enabling the pressurizing chamber to receive fresh treatment fluid in a receiving mode. When the drive pressure in the pressurizing chamber reaches a predetermined pressure value correlated to the volume of fresh treatment fluid in the pressurizing chamber, the flow control assembly automatically transitions to a discharging mode, wherein both the drive fluid outlet valve and the treatment fluid inlet valve assume a closed position. As a result the fresh treatment fluid is driven from the pressurizing chamber into the pad where it displaces treatment fluid residing therein.

25 Claims, 10 Drawing Sheets

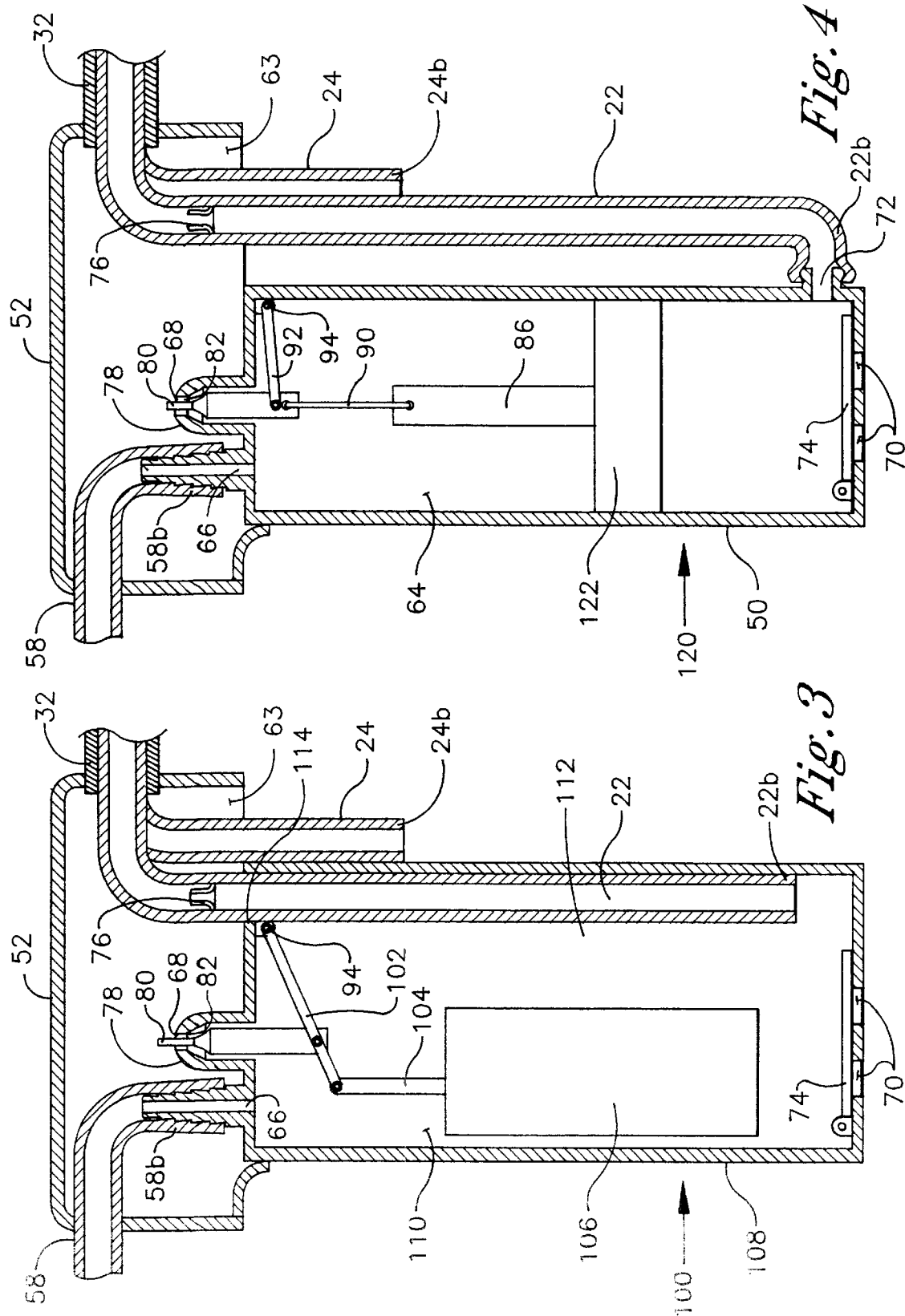

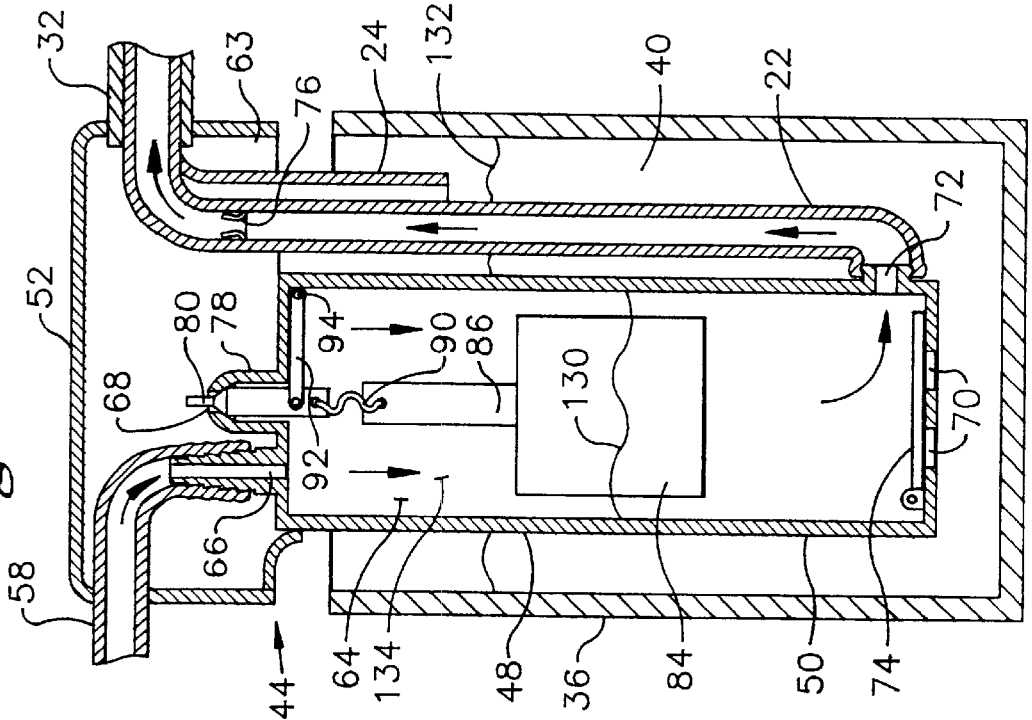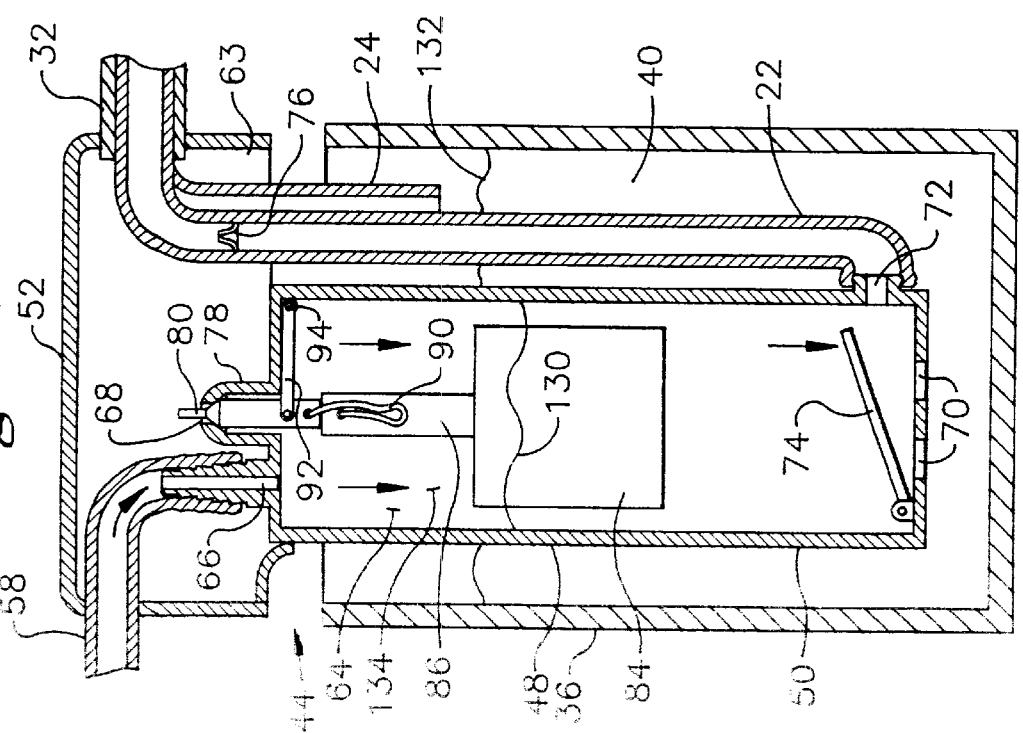

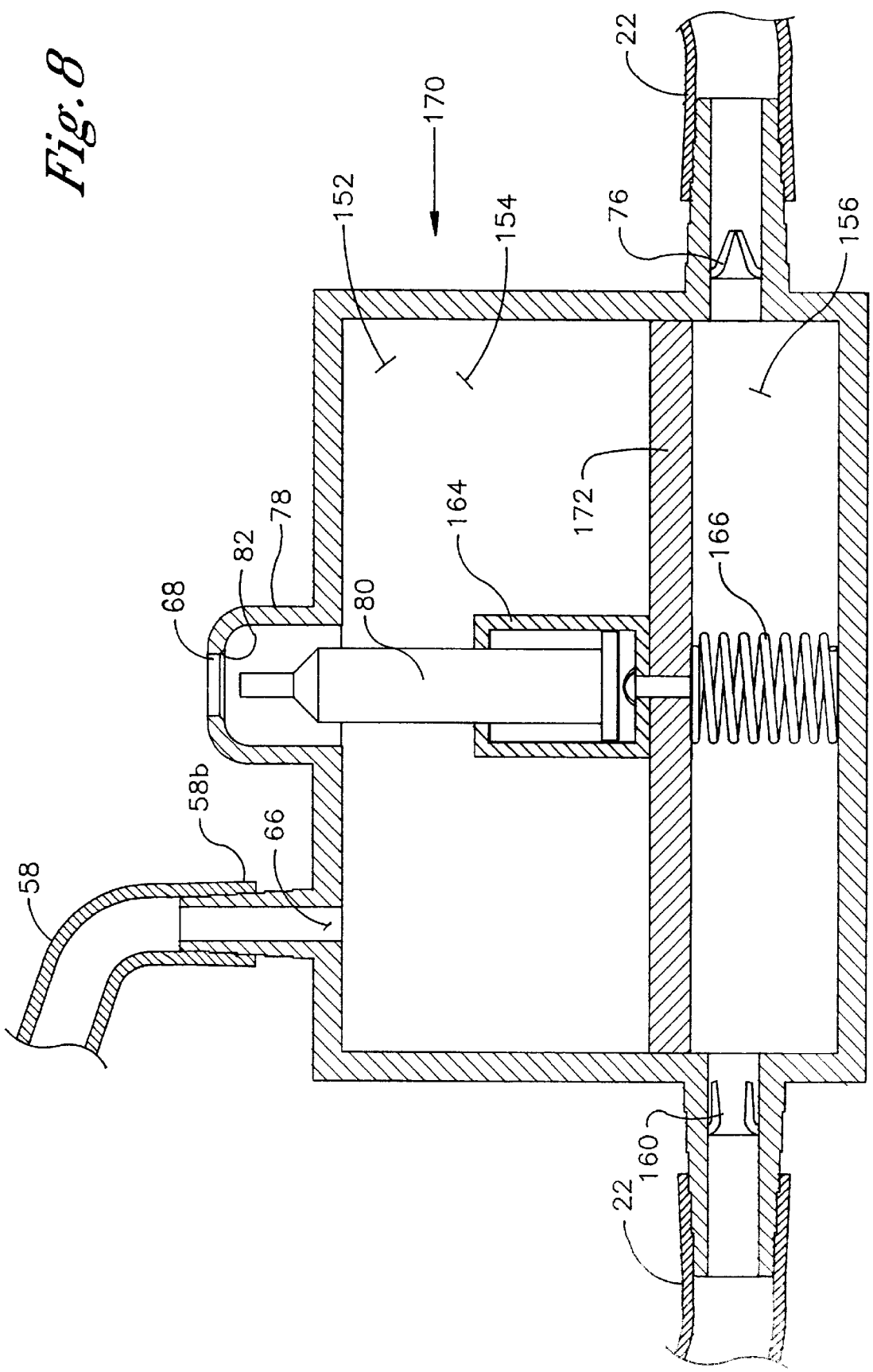

FLUID DRIVE MECHANISM FOR A THERAPEUTIC TREATMENT SYSTEM

TECHNICAL FIELD

The present invention relates generally to therapeutic treatment of the body and particularly to therapeutic treatment of the body provided by circulating a nonambient temperature treatment fluid over an affected body surface. More particularly, the invention relates to a mechanism for driving the fluid through a treatment pad of a therapeutic treatment system positioned on the body.

BACKGROUND OF THE INVENTION

Bodily injuries and ailments are commonly treated by applying a nonambient temperature material to the affected area of the body. For example, a low temperature material, typically applied in the form of ice or a cold liquid, may advantageously inhibit swelling in the region of the injury. A high temperature material, typically applied in the form of hot water or an active heating element, may advantageously reduce pain and promote healing. A number of splint devices are known in the art for applying nonambient temperature materials to injured or otherwise ailing areas of the body as evidenced by U.S. Pat. No. 3,548,819 to Davis et al; U.S. Pat. No. 3,901,225 to Sconce; and U.S. Pat. No. 4,706,658 to Cronin. One disadvantage of such devices is that the low temperature materials become warmer as they remain in contact with the body during treatment and the body transfers heat to the low temperature materials. Conversely, high temperature materials become cooler as they transfer heat to the body. This disadvantage can be remedied by periodically replacing the nonambient temperature materials. However, constant replenishment of these materials is cumbersome and inconvenient, and results in periodic treatment temperature fluctuations.

In response to this problem, a number of systems have been developed for continuously circulating a cooling fluid from a low temperature reservoir to a desired body location. Such systems are typified by U.S. Pat. No. 2,726,658 to Chessey; U.S. Pat. No. 3,683,902 to Artemenko et al; and U.S. Pat. No. 4,962,761 to Golden. These fluid circulation systems in general are relatively complex, rendering them costly to manufacture and maintain, as well as difficult to operate. Accordingly, the systems are not practical for widespread use.

U.S. Pat. No. 5,241,951 to Mason et al, incorporated herein by reference, discloses a therapeutic treatment system which rectifies the shortcomings of the above-referenced fluid circulation systems. The therapeutic treatment system of U.S. Pat. No. 5,241,951 is relatively simple, rendering it less costly to manufacture and maintain and enabling greater ease of operation than the prior systems. The system of U.S. Pat. No. 5,241,951 consists essentially of a fluid reservoir, a submersible pump, a pad having an internal fluid flowpath, fluid inlet and outlet lines connecting the pad to the pump and an in-line flow control valve. The system is operated by filling the reservoir with a nonambient temperature treatment fluid and submersing the pump in the fluid. The pad is positioned on the desired treatment region of the user and the pump is activated to deliver fresh treatment fluid from the reservoir to the pad via the fluid inlet line and return spent treatment fluid from the pad to the reservoir via the fluid outlet line. The user regulates the temperature of the pad by manually adjusting the valve to control the flow rate of fluid through the pad.

The system of U.S. Pat. No. 5,241,951 has been shown to provide effective therapeutic treatment to the body. Nevertheless, it has been found that the performance of the system is limited by the submersible pump. In particular, submersible pumps providing the required degree of reliability, i.e., durability and longevity, for the therapeutic treatment application of U.S. Pat. No. 5,241,951 are costly relative to the other system components. In addition, the electric motor of the submersible pump generates heat which is undesirably transferred to the cooling fluid in which the pump is submersed. Also submersion of the electrically-powered pump in the cooling fluid raises safety concerns for the user. Accordingly, the present invention recognizes the need for an improved fluid drive mechanism utilized within a fluid circulation-type therapeutic treatment system. It is an object of the present invention to provide a fluid drive mechanism for a therapeutic treatment system which is effective, safe and reliable, yet relatively inexpensive. It is another object of the present invention to provide a fluid drive mechanism which provides ease of operation and control for the user. These objects and others are achieved in accordance with the invention described hereafter.

SUMMARY OF THE INVENTION

The present invention is a fluid drive mechanism for conveying a nonambient temperature stored treatment fluid employed in a therapeutic treatment system. The fluid drive mechanism conveys the stored treatment fluid from a treatment fluid storage vessel to a treatment pad. The pad is positionable on a desired portion of the body and has a pad inlet, a pad outlet, and a continuous pad flowpath from the pad inlet to the pad outlet. A pad inlet line is connected to the pad inlet and a pad outlet line is connected to the pad outlet.

The fluid drive mechanism has a drive fluid pump and a pressurizing chamber. The pressurizing chamber has a drive fluid inlet for receiving a pressurized drive fluid from the drive fluid pump, a drive fluid outlet for periodically discharging the pressurized drive fluid to the atmosphere, a treatment fluid inlet for periodically receiving the stored treatment fluid from the treatment fluid storage vessel, and a treatment fluid outlet for periodically discharging the stored treatment fluid into the pad inlet line and thereafter to the pad flowpath where the stored treatment fluid displaces the treatment fluid already residing in the pad flowpath. The displaced treatment fluid from the pad flowpath is returned to the treatment fluid storage vessel by the pad outlet line. The receiving and discharging modes of operation occur sequentially and continuously to provide the fluid drive mechanism with a plurality of operating cycles in series.

The drive fluid outlet is fitted with a drive fluid outlet valve which enables the fluid drive mechanism to transition between the receiving and discharging modes of operation. In particular, the drive fluid outlet valve selectively controls discharge of the drive fluid from the pressurizing chamber to the atmosphere. The drive fluid outlet valve opens when a predetermined substantial volume decrease of stored treatment fluid occurs in the pressurizing chamber, which creates a pressure drop enabling stored treatment fluid to enter the pressurizing chamber from the treatment fluid storage vessel. Conversely, the drive fluid outlet valve closes when a predetermined substantial volume increase of stored treatment fluid occurs in the pressurizing chamber, which creates a pressure buildup driving stored treatment fluid from the pressurizing chamber to the pad flowpath. Thus, opening the drive fluid outlet valve transitions the fluid drive mechanism to the receiving mode of operation and closing the drive fluid outlet valve transitions the fluid drive mechanism to the discharging mode of operation. Since the drive fluid outlet valve opens and closes in response to the volume of stored treatment fluid in the pressurizing chamber, the operating modes of the fluid drive mechanism are likewise correlated to the volume of stored treatment fluid in the pressurizing chamber. It is also noted that the treatment fluid inlet is fitted with a treatment fluid inlet valve to substantially inhibit back flow of the stored treatment fluid from the pressurizing chamber to the treatment fluid storage vessel.

A number of alternate embodiments are employed in the present fluid drive mechanism to effect opening and closing of the drive fluid outlet valve in response to the volume of stored treatment fluid in the pressurizing chamber. In accordance with each of these embodiments, a displacement member is positioned within the pressurizing chamber and is displaced in response to changes in the stored treatment fluid volume or the drive fluid pressure. Displacing the displacement member to a maximum downward level actuates opening of the drive fluid outlet valve, while displacing the displacement member to a maximum upward level actuates closing of the drive fluid outlet valve. In accordance with one embodiment, the displacement member is a buoyant float which need not engage the walls of the pressurizing chamber. In accordance with another embodiment, the displacement member is a piston which slidably engages the walls of the pressurizing chamber. In accordance with yet another embodiment, the displacement member is a flexible diaphragm which is anchored to the walls of the pressurizing chamber.

The invention will be further understood from the accompanying drawings and description.

BRIEF DESCRIPTION OF THE DRAWINGS

FIG. 3 is a partial cross-sectional view of an alternate embodiment of a flow control assembly included within the fluid drive mechanism of FIG. 1.

FIG. 4 is a partial cross-sectional view of yet another alternate embodiment of a flow control assembly included within the fluid drive mechanism of FIG. 1.

FIGS. 5A–5D are partial cross-sectional views of the flow control assembly of FIG. 2 in a series of operating modes comprising a single operating cycle.

FIG. 8 is a partial cross-sectional view of an alternate embodiment of a flow control assembly included within the fluid drive mechanism of FIG. 6.

DESCRIPTION OF PREFERRED EMBODIMENTS

Figure 1:
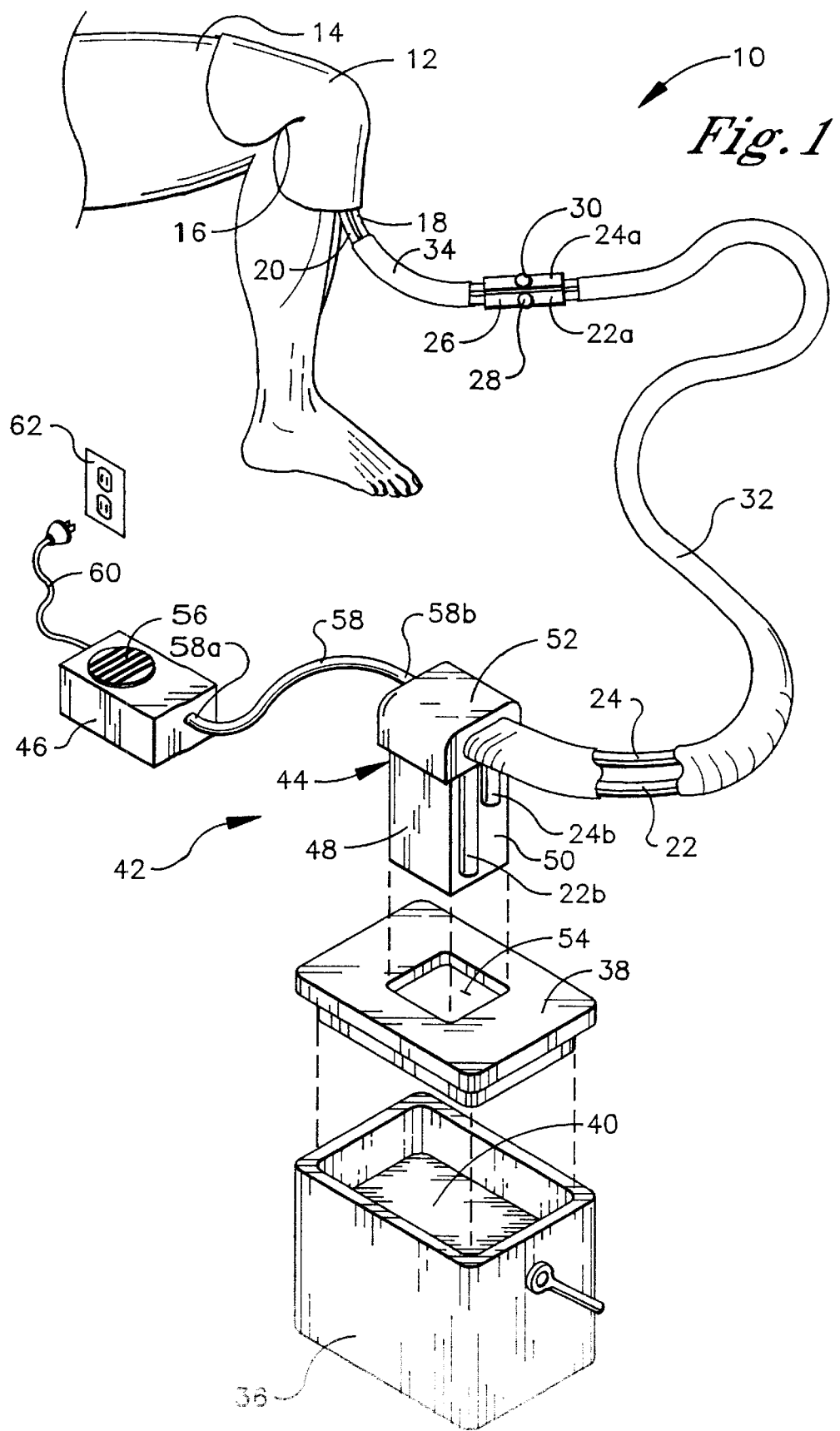
FIG. 1 is a perspective view of a therapeutic treatment system including a partially exploded view of a fluid drive mechanism of the present invention.

Referring initially to FIG. 1, a therapeutic treatment system including a fluid drive mechanism is shown and generally designated 10. For purposes of illustration, the therapeutic fluid circulation system 10 is described below as used in low temperature cooling applications. However, it is apparent to the skilled artisan that the system 10 can be adapted for high temperature heating applications simply by substituting a high temperature treatment fluid for the low temperature treatment fluid described hereafter.

The system 10 comprises a treatment pad 12 positionable on the body of a patient at the point where therapeutic cooling treatment is desired. The treatment pad 12 is shown positioned on the knee 14, but it is understood that the pad 12 can alternatively be positioned substantially anywhere on the body where the treatment is desired. The treatment pad 12 is preferably a substantially planar member made up of a thin flexible heat-conductive material, forming a bladder which encloses an internal flowpath for the treatment fluid. Although not shown, the flowpath can contain a plurality of baffles to increase the tortuosity of the flowpath. The treatment pad 12 is readily conformable to the body contours of the patient, having a plurality of slits 16 formed therein to enhance conformance. Treatment pads of the type having utility in the present system 10 are disclosed in U.S. Pat. No. 5,417,720, incorporated herein by reference.

The treatment pad 12 has a pad inlet port 18 and a pad outlet port 20 connected to a pad inlet line 22 and a pad outlet line 24, respectively. The pad inlet and outlet lines 22, 24 and pad inlet and outlet ports 18, 20 have substantially the same inside diameter and are connected at a joint 26 having snap-action locking inlet and outlet couplings 28, 30 which are manually selectively releasable. More specifically, the pad inlet port 18 is connected to the proximal end of 22a of the pad inlet line 22 by means of the inlet coupling 28 and the pad outlet port 20 is connected to the proximal end 24a of the pad outlet line 24 by means of the outlet coupling 30. The terms "proximal" and "distal" are used herein relative to the treatment pad 12.

An insulative sheath 32 covers the pad inlet and outlet lines 22, 24 (shown in cut-away), enclosing the lines 22, 24 in a single tubular unit. The sheath 32, pad inlet line 22 and pad outlet line 24 are formed from supple materials which render them fully flexible. The sheath 32 has a strong and resilient plastic exterior skin and an insulating foam interior which minimizes heat exchange between the pad inlet line 22 and the pad outlet line 24 or between the lines 22, 24 and the surrounding environment. The sheath 32 also prevents condensate formation on the exterior of the pad inlet and outlet lines 22, 24. An insulative sheath 34 having a similar composition can also be provided over the fluid inlet and outlet ports 18, 20 extending between the joint 26 and the treatment pad 12.

The therapeutic treatment system 10 has a treatment fluid storage vessel 36 which is preferably a fluid-tight, thermally-passive container, such as a conventional insulated plastic picnic cooler. The term "thermally passive", as used herein, characterizes a structure which is free of any active cooling elements, such as refrigeration coils or the like. Thus, the entirety of the therapeutic treatment system 10 is likewise characterized as thermally passive. The treatment fluid storage vessel 36 serves as a fresh storage reservoir, having a selectively removable cover 38 for the addition of fresh treatment fluid into the vessel 36 or the withdrawal of stored treatment fluid 40 from the vessel 36. The cover 38 aids in maintaining the low temperature of the stored treatment fluid 40 in the treatment fluid storage vessel 36. The stored treatment fluid 40 is a low temperature fluid, i.e., below ambient room temperature, and preferably a cold liquid.

The system 10 further comprises a fluid drive mechanism generally designated 42 which includes a flow control assembly 44 and a pump 46. The treatment fluid storage vessel 36, cover 38, and flow control assembly 44 are shown in an exploded view for purposes of illustration. It is understood that these components are assembled with one another in a manner described hereafter to provide the system 10 with an integrated structure during operation. The flow control assembly 44 has a housing 48 formed from a durable, water-proof, rigid, hard plastic which encloses the internal components of the flow control assembly 44. The housing 48 includes a lower section 50 and an attached upper section 52, wherein the upper section 52 has a wider cross section than the lower section 50. An aperture 54 is provided in the cover 38 of the treatment fluid storage vessel 36. The aperture 54 has a cross section wider than that of the lower section 50, but narrower than that of the upper section 52. When the system 10 is assembled for operation, the narrower lower section 50 is received through the aperture 54 and extends into the treatment fluid storage vessel 36, while the wider upper section 52 is retained atop the cover 38 external to the treatment fluid storage vessel 36 because of its wider cross section.

The pump 46 is substantially any means for compressing a drive fluid received into the pump 46 via a pump inlet port 56 and delivering the pressurized drive fluid to the flow control assembly 44 via a drive fluid line 58. The drive fluid is preferably an ambient temperature gas and is more preferably ambient temperature air drawn into the pump inlet port 56 from the surrounding environment and discharged from the pump 46 via the end 58a of the drive fluid line 58 engaging the pump 46. A preferred pump having utility in the present system 10 is a conventional electrically-powered air pump, such as is typically used in small household aquarium applications. The preferred pump is driven by an ac-powered, single-speed electric motor (not shown) having an external power line 60 connectable to an ac power source via a conventional ac wall outlet 62.

Although a preferred pump is described above, the present invention is not limited to any one type of pump. For example, the pump can alternatively be an ac-powered, variable-speed pump. In other alternatives, the pump can be a dc-powered, variable- or single-speed pump employing a transformer to convert the ac power from the ac wall outlet 62 to dc power. The dc-powered pump can alternatively obtain its power directly from a dc power source, such as an automobile battery or a portable external or internal battery pack consisting of one or more disposable dry cell batteries or rechargeable batteries. In still another alternative, the pump can be a canister (not shown) of a compressed gas, such as carbon dioxide, which serves as the drive fluid. The cannister is in fluid communication with the pressurizing chamber 64 via a regulator valve positioned across the drive fluid line 58. In yet another alternative, the pump can be a manually operated pump. Manually operated pumps, such as a bulb-type pump commonly used in an arm cuff for blood pressure measuring applications, are well known to the skilled artisan. A manually operated pump is the preferred pump of the therapeutic treatment system 10 when an electric power source or compressed gas cannister is unavailable.

Figure 2:
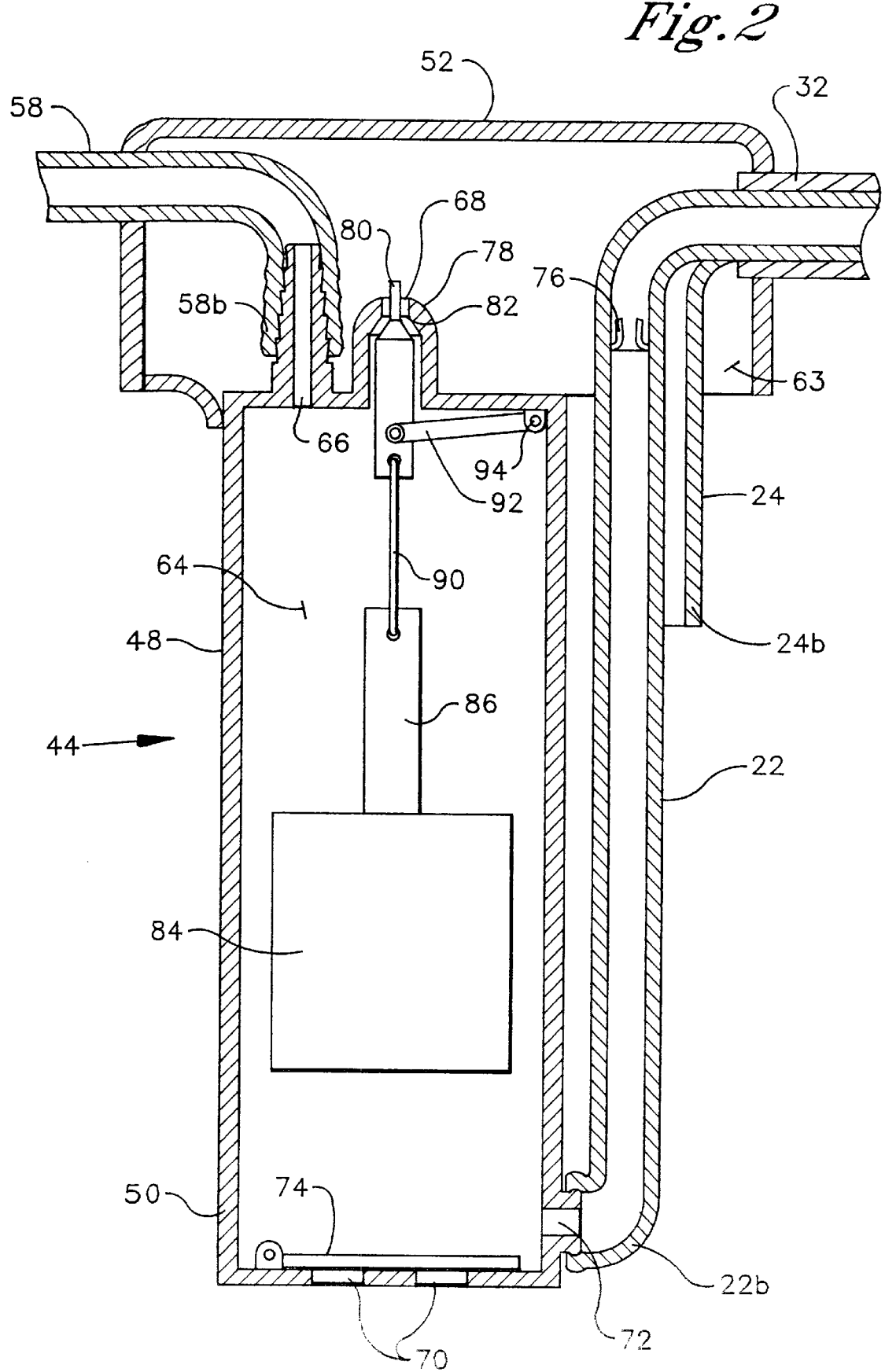
FIG. 2 is a partial cross-sectional view of a flow control assembly included within the fluid drive mechanism of FIG. 1.

Referring to FIG. 2, the flow control assembly 44 is described in further detail. The upper section 52 of the housing 48 is open to the atmosphere through a vent 63, while the lower section 50 encloses a fluid-tight pressurizing chamber 64. The upper section 52, in cooperation with the lower section 50, serves generally as a mount which maintains the flow control assembly 44 in engagement with the treatment fluid storage vessel 36 and in proper position with relation to the stored treatment fluid 40 in the treatment fluid storage vessel 36. The upper section 52 also serves as a guide for the distal ends 22b, 24b of the pad inlet and outlet lines 22, 24, respectively, and for the end 58b of the drive fluid line 58 opposite the pump 46. The upper section 52 receives and retains each of the lines 22, 24, 58. The lower section 50 defines the walls of the pressurizing chamber 64 which are rigidly configured and have a fixed geometry. The pressurizing chamber 64 is essentially impermeable to the stored treatment fluid 40 or the drive fluid with the exception of controlled fluid flow permitted through drive fluid inlet and outlet ports and treatment fluid inlet and outlet ports as described hereafter.

The drive fluid inlet port 66 is a first opening in the top of the lower section 50 which engages the end 58b of the drive fluid line 58. The drive fluid outlet port 68 is a second opening in the top of the lower section 50 of the housing 48 adjacent to the drive fluid inlet port 66. The treatment fluid inlet port 70 is a plurality of first openings in the bottom of the lower section 50. The treatment fluid outlet port 72 is a second opening in the bottom of the lower section 50 adjacent to the treatment fluid outlet port 72 which engages the distal end 22b of the pad inlet line 22.

A flapper valve 74 is positioned at the treatment fluid inlet port 70, functioning as a treatment fluid inlet valve to selectively permit flow of treatment fluid 40 from the treatment fluid storage vessel 36 into the pressurizing chamber 64 or prevent back flow of treatment fluid 40 from the pressurizing chamber 64 into the treatment fluid storage vessel 36. A check valve 76 is intermediately positioned within the pad inlet line 22, functioning as a treatment fluid outlet valve to selectively permit flow of treatment fluid 40 into the pad 12 from the pressurizing chamber 64 via the distal end 22b of the pad inlet line 22 or to prevent back flow of treatment fluid 40 into the pressurizing chamber 64 from the treatment pad 12. Although not shown, the pad outlet line 24 has a flow restriction positioned at some point in the pad outlet line 24 or pad outlet port 20. The flow restriction can be substantially any element which restricts the cross-sectional area of the pad outlet line 24 or pad outlet port 20, such as a reduction orifice, a crimp in the line, a pressure relief valve or a selectively adjustable valve. Alternatively, the flow restriction can be provided by sizing the pad outlet line 24 smaller than the pad inlet line 22.

The flow restriction in the pad outlet line 24 or pad outlet port 20 creates a back pressure in the treatment pad 12 which is desirable for effective operation of the therapeutic treatment system 10. It is also apparent that the flow restriction can be effectively employed to directly control the flow rate of the stored treatment fluid 40 from the pressurizing chamber 64 through the treatment pad 12, and hence control the temperature of the treatment pad 12. Alternatively, a flow restriction can be placed in the pad inlet line 22 or pad inlet port 18, such as the selectively adjustable valve disclosed in U.S. Pat. No. 5,241,951, to directly control the flow rate of the stored treatment fluid 40 from the pressurizing chamber 64 through the treatment pad 12

The drive fluid line 58 opens into the pressurizing chamber 64 via the drive fluid inlet port 66. Drive fluid flow into the pressurizing chamber 64 is controlled by operation of the pump 46, either increasing or decreasing the pump speed and correspondingly the drive fluid flow rate, if the pump 46 is adjustable, or initially sizing the pump for a desired drive fluid flow rate, if the pump 46 is not adjustable. Alternatively, a fixed or selectively adjustable flow restriction (not shown) can be positioned in the drive fluid line 58 to control the drive fluid flow rate into the pressurizing chamber 64. As will be apparent below in describing operation of the fluid drive mechanism 42, the flow rate of the stored treatment fluid 40 from the pressurizing chamber 64 through the treatment pad 12 can be controlled indirectly by controlling the drive fluid flow rate using one of the above-described techniques. These indirect techniques are an alternative to the direct techniques described above for controlling the treatment fluid flow rate through the treatment pad 12.

A drive fluid outlet valve 78 is positioned in the drive fluid outlet port 68 to selectively permit or prevent drive fluid flow from the pressurizing chamber 64 into the surrounding atmosphere. The drive fluid outlet valve 78 comprises a valve pin 80 selectively displaceable against a valve seat 82 which is the perimeter of the drive fluid outlet port 68. The free cross-sectional area of the drive fluid outlet port 68 is substantially greater than the free cross-sectional area of the drive fluid inlet port 66 when the drive fluid outlet valve 78 is open. A displacement member 84 enclosed within the pressurizing chamber 64 is provided to actuate the drive fluid outlet valve 78. The displacement member 84 is either hollow or formed from a relatively low density material such that the displacement member 84 is substantially buoyant in the stored treatment fluid 40, functioning as a float. In the present embodiment, the displacement member 84 is a rigid body having a substantially fixed geometry which approximates the cross section of the pressurizing chamber 64, but is slightly smaller, so that vertical displacement of the displacement member 84 within the pressurizing chamber 64 is not substantially impeded by the sides of the lower section 50, nor is flow of the stored treatment fluid 40 and drive fluid between the displacement member 84 and the sides of the lower section 50 blocked.

The displacement member 84 is provided with an upper extension 86 which is connected to the valve pin 80 by a connective member 90. The connective member 90 is a flexible link such as a length of string, cord or chain. The valve pin 80 is rotatably joined to one end of a rigid alignment arm 92 and the opposite end of the alignment arm 92 is rotatably joined to a pivot 94 which is integral with the top of the lower section 50. The alignment arm 92 rotates about the valve pin 80 and pivot 94 in correspondence with vertical movement of the valve pin 80 up and down. The alignment arm 92 maintains the alignment of the valve pin 80 with respect to the drive fluid outlet port 68 as the valve pin 80 moves vertically.

It is apparent from the present construction that when the displacement member 84 of the drive fluid outlet valve 78 is displaced upward, the displacement member 84 ultimately reaches an upward transition level where the upper extension 86 is in abutment with the valve pin 80 and the connective member 90 is relaxed. Once this upward transition level is reached, continued upward displacement of the displacement member 84 to a maximum upward level causes the upper extension 86 to urge the valve pin 80 upward into the valve seat 82 closing the drive fluid outlet valve 78. Conversely, when the displacement member 84 is displaced downward, the displacement member 84 ultimately reaches a downward transition level where the upper extension 86 separates from the valve pin 80 by a length corresponding to that of the connective member 90 and the connective member 90 is pulled taut. Once this downward transition level is reached, continued downward displacement of the displacement member 84 to a maximum downward level causes the connective member 90 to pull the valve pin 80 downward away from the valve seat 82 reopening the drive fluid outlet valve 78. Alignment of the upper extension 86 with the valve pin 80 is maintained during vertical displacement of the displacement by the close spatial relation between the displacement member 84 and the lower section 50. In contrast to the drive fluid outlet valve 78, both the flapper valve 74 and check valves 76 are passive valves which only operate in response to pressure changes caused by the action of the drive fluid outlet valve 78, as will be apparent below in describing operation of the fluid drive mechanism 42.

Referring to FIG. 3, an alternate embodiment of the flow control assembly is shown and generally designated 100. The flow control assembly 100 has a number of components substantially identical to those of FIG. 2 which are identified in FIG. 3 by the same reference characters as FIG. 2. The flow control assembly 100 differs from the flow control assembly 44 primarily in the characteristics of the lower section and the connective and displacement members. The connective member 102 of the flow control assembly 100 is a rigid lever arm having a construction similar to the alignment arm 92. The connective member 102 is rotatably connected at one end to the pivot 94 and rotatably connected at the opposite end to the upper extension 104 while an intermediate point of the connective member 102 is rotatably connected to the valve pin 80. The upper extension 104 is positioned on the displacement member 106 out of direct alignment with the valve pin 80. The displacement member 106 and lower section 108 are dimensioned such that the displacement member 106 has a cross section substantially less than the cross section of the pressurizing chamber 110. This configuration provides a substantial annular space 112 in the pressurizing chamber 110 between the displacement member 106 and lower section 108. The pad inlet line 22 enters the pressurizing chamber 110 through a third opening 114 in the top of the lower section 108 and extends through the annular space 112 to the bottom of the pressurizing chamber 110. The distal end 22b of the pad inlet line 22 serves as the treatment fluid outlet port and no second opening is provided in the bottom of the lower section 108.

It is apparent from the present construction that when the displacement member 106 of the drive fluid outlet valve 78 is displaced upward, the displacement member 106 ultimately reaches an upward transition level where the connective member 102 begins to upwardly displace the valve pin 80 as it rotates in a first direction. Once this upward transition level is reached, continued upward displacement of the displacement member 106 to a maximum upward level causes the connective member 102 to urge the valve pin 80 upward into the valve seat 82 closing the drive fluid outlet valve 78. Conversely, when the displacement member 106 is displaced downward, the displacement member 106 ultimately reaches a downward transition level where the connective member 102 begins to downwardly displace the valve pin 80 as it rotates in a second direction substantially opposite the first direction. Once this downward transition level is reached, continued downward displacement of the displacement member 106 to a maximum downward level causes the connective member 102 to pull the valve pin 80 downward away from the valve seat 82 reopening the drive fluid outlet valve 78. Alignment of the displacement member 106 within the pressurizing chamber 110 is maintained by the connective member 102.

Referring to FIG. 4, another alternate embodiment of the flow control assembly is shown and generally designated 120. The flow control assembly 120 has a number of components substantially identical to those of FIG. 2 which are identified in FIG. 4 by the same reference characters as FIG. 2. The flow control assembly 120 differs from the flow control assembly 44 primarily in the characteristics of the displacement member. The displacement member 122 of the flow control assembly 120 is a piston formed from a material which may or may not be buoyant in the stored treatment fluid 40. In either case, the displacement member 122 and lower section 50 are dimensioned such that the displacement member 122 has a cross section nearly the same as the cross section of the pressurizing chamber 64, but incrementally smaller. The cross section of the displacement member 122 is incrementally smaller only by a sufficient degree to enable slidable displacement of the displacement member 122 relative to the lower section 50, while maintaining a fluid seal between the displacement member 122 and the lower section 50. This configuration enables the flow control assembly 120 to establish a pressure differential on opposite sides of the displacement member 122 within the pressurizing chamber 64. It is apparent from the present construction that the displacement member 122 effects opening and closing of the drive fluid outlet valve 78 in substantially the same manner as the drive fluid outlet valve 78 of FIG. 2 except that the displacement member 122 is driven primarily by the pressure of the stored treatment fluid 40 or drive fluid on the displacement member 122 in the pressurizing chamber 64 (particularly where the displacement member 122 is not buoyant in the stored treatment fluid 40), while the displacement member 84 is driven primarily by the buoyant force of the stored treatment fluid 40 on the displacement member 84 in the pressurizing chamber 64.

Three alternate embodiments of flow control assemblies 44,100,120 have been shown above. It is apparent to the skilled artisan from this teaching that other embodiments of flow control assemblies are possible within the scope of the present invention by configuring the elements of the flow control assemblies 44, 100, 120 in alternate combinations not expressly shown herein. For example, the connective member 102 of the flow control assembly 100 can be combined with the displacement member 122 and lower section 50 of the flow control assembly 120 to achieve another alternate flow control assembly within the scope of the present invention. Similarly, the connective member 90 of the flow control assembly 44 can be combined with the displacement member 106 and lower section 108 of the flow control assembly 100 to achieve still another alternate flow control assembly within the scope of the present invention. In this embodiment it may be desirable to further modify the displacement member 106, coupling it with a vertical displacement guide, such as a rail, within the pressurizing chamber 110 to maintain the desired alignment of the upper extension and valve pin 80.

Operation of the flow control assemblies 44, 100, 120 is substantially similar. For purposes of illustration, a method of operation is described below for the flow control assembly 44 as utilized within the fluid drive mechanism 42 and, more generally, as utilized within the therapeutic treatment system 10. However, it is readily within the purview of the skilled artisan to adapt the following operating method to the alternate flow control assemblies 100, 120 described above or to other flow control assemblies which are within the scope of the present invention.

Referring to FIGS. 1 and 5A–5D, operation of the therapeutic treatment system 10 employing the fluid drive mechanism 42 is initiated by filling the treatment fluid storage vessel 36 with a fresh cold treatment fluid 40 from a remote source (not shown). The fresh cold treatment fluid 40 is preferably ice water at a temperature approaching its freezing point. After filling the treatment fluid storage vessel 36 with a desired volume of the fresh cold treatment fluid 40, which is several times greater than the volumetric capacity of the flowpath within the treatment pad 12, the cover 38 is positioned on the treatment fluid storage vessel 36 to reduce heat loss from the cold treatment fluid 40 to the surrounding atmosphere. The joint 26 is secured and the treatment pad 12 is placed on the skin of the patient at the point on the body where therapeutic treatment is desired and preferably secured to the body by a wrap or straps integral with the construction of the treatment pad 12. An additional padding material, such as a soft cloth, can be placed on the skin between the treatment pad 12 and the skin for the comfort of the patient or such padding material can be integral with the construction of the treatment pad 12. Typically residual ambient temperature treatment fluid is already present in the flowpath of the treatment pad 12 from a prior treatment.

Figure 5A:
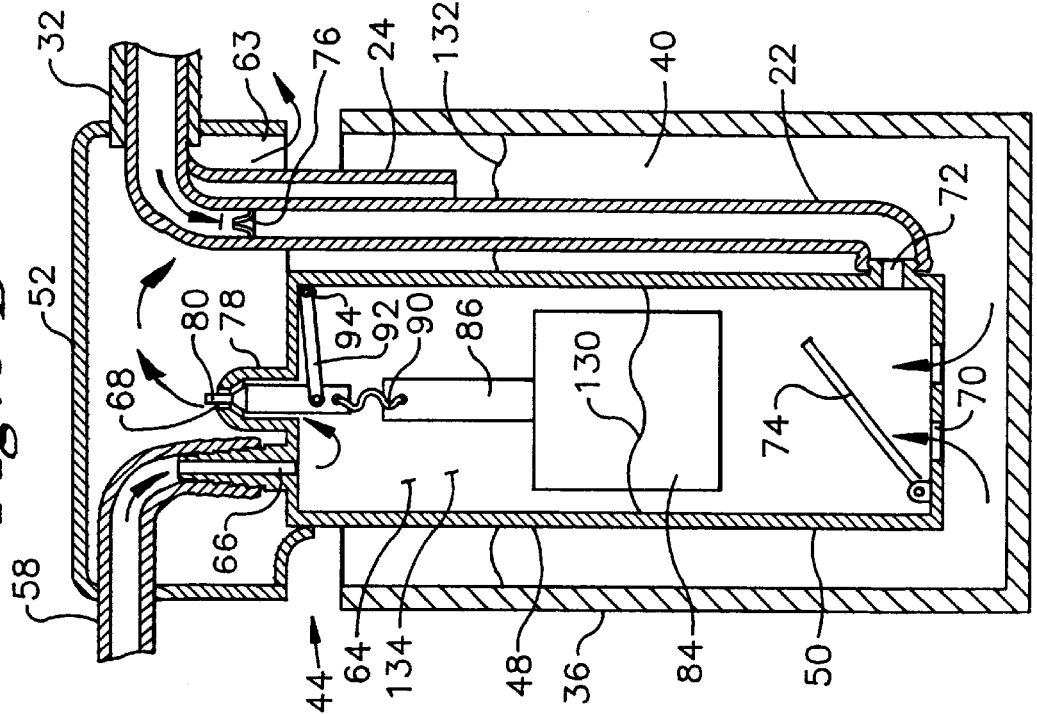

The flow control assembly 44 is positioned in close fitting engagement with the cover 38 by placing the lower section 50 of the housing 48 through the aperture 54 so that it extends into the treatment fluid storage vessel 36, while the upper section 52 of the housing 48 remains fixedly positioned atop the cover 38. The system 10 is activated by connecting the external power line 60 to the ac wall outlet 62, actuating the pump 46 in continuous uninterrupted operation. FIG. 5A shows the flow control assembly 44 at the outset of an operating cycle. Specifically, FIG. 5A shows the flow control assembly 44 at the precise time when the assembly 44 has just completed the treatment fluid discharging mode of operation and is transitioning to the treatment fluid receiving mode of operation. It is noted that the terms "discharging" and "receiving" as used herein are only with reference to flow of the stored treatment fluid 40 through the pressurizing chamber 64. The terms are not used to reference the flow of treatment fluid 40 through the treatment pad 12 because the treatment pad 12 is simultaneously in the receiving and discharging modes of operation when the flow control assembly 44 is in the discharging mode of operation. The treatment pad 12 is essentially inactive when the assembly 44 is in the receiving mode of operation except for a minor volume of warmer treatment fluid which preferably continuously leaks from the treatment pad 12 through the open flow restriction in the pad outlet line 24.

At the outset of the receiving mode of operation, the low treatment fluid level 130 in the pressurizing chamber 64 has just dropped the displacement member 84 to a maximum downward level toward the bottom of the pressurizing chamber 64. The valve pin 80 has transitioned to an open position below the valve seat 82 in response to the downward pulling force of the taut connective member 90 which results from the low treatment fluid level 130. The pressurized drive fluid, preferably air, is fed by the continuously-operating pump 46 into the pressurizing chamber64 via the drive fluid line 58. However, the pressurizing chamber 64 remains substantially at ambient atmospheric pressure because the pressurized drive fluid immediately exits the pressurizing chamber 64 via the open drive fluid outlet valve 78 into the surrounding atmosphere. Drive fluid flow is indicated by the directional arrows. As noted above, the free cross-sectional area of the drive fluid outlet port 68 is substantially greater than the free cross-sectional area of the drive fluid inlet port 66 when the drive fluid outlet valve 78 is open, preventing a substantial pressure buildup in the pressurizing chamber 64 during the receiving mode.

The check valve 76 is going from the open position to the closed position in response to the pressure drop in the pressurizing chamber and the treatment fluid back pressure in the treatment pad 12. The treatment fluid back pressure is substantially greater than the hydrostatic head of the treatment fluid level 130 in the pressurizing chamber 64. Thus, the check valve 76 prevents the back flow of treatment fluid 40 from the treatment pad 12 into the pressurizing chamber 64 via the pad inlet line 22 when the pressurizing chamber 64 is at ambient pressure. The flapper valve 74 is going from the closed position to the open position in response to an upward force through the treatment fluid inlet port 70 produced by the hydrostatic head of the treatment fluid level 132 in the treatment fluid storage vessel 36 indicated by the directional arrows.

Figure 5B:
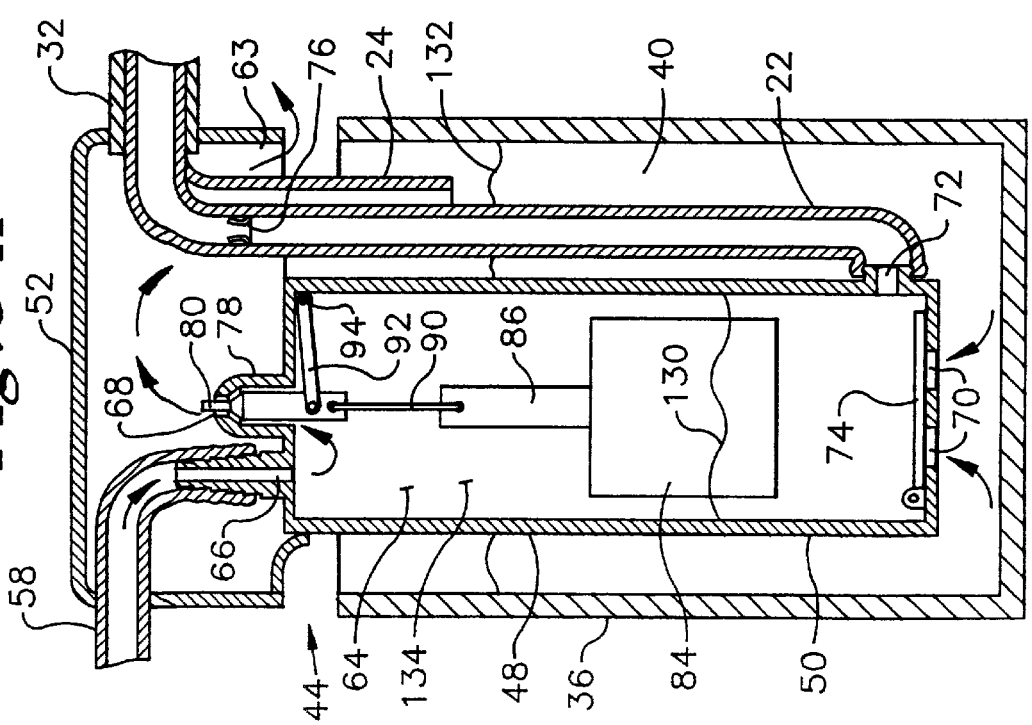

FIG. 5B shows the flow control assembly 44 at an intermediate point in the treatment fluid receiving mode of operation. The hydrostatic head of the treatment fluid level 132 in the treatment fluid storage vessel 36 has more fully opened the flapper valve 74 enabling a significant volume of treatment fluid 40 to enter the pressurizing chamber 64 from the treatment fluid storage vessel 36. It is noted that a conventional stop (not shown) is provided in association with the flapper valve 74 to restrict the flapper valve 74 from opening too far, i.e., 90° or more. As the treatment fluid 40 enters the pressurizing chamber 64, the treatment fluid level 130 in the pressurizing chamber 64 rises. However, the treatment fluid level 132 in the treatment fluid storage vessel 36 does not drop significantly due to the relative volume disparity between the treatment fluid storage vessel 36 and the pressurizing chamber 64. Treatment fluid flow is indicated by the directional arrows. The stored treatment fluid 40 entering the pressurizing chamber 64 displaces the displacement member 84 upward as the result of buoyant forces, partially relaxing the connective member 90 and causing it to randomly coil. However, the valve pin 80 stays in the open position below the valve seat 82 due to the absence of any significant upward force on the valve pin 80. Thus, the pressurized drive fluid continues to pass from the drive fluid line 58 through the pressurizing chamber 64, indicated by the directional arrows, and the pressurizing chamber 64 remains at ambient atmospheric pressure. The check valve 76 in the pad inlet line 22 remains closed in response to the treatment fluid back pressure in the treatment pad 12.

FIG. 5C shows the flow control assembly 44 at the precise time when the flow control assembly 44 has just completed the treatment fluid receiving mode of operation and is transitioning to the treatment fluid discharging mode of operation. At the outset of the discharging mode of operation, the high treatment fluid level 130 in the pressurizing chamber 64 and the resulting increased buoyant force has just raised the displacement member 84 to a maximum upward level toward the top of the pressurizing chamber 64. The valve pin 80 has transitioned to a closed position in the valve seat 82 in response to the upward pushing force of the upper extension 86 abutting the valve pin 80 which results from the high treatment fluid level 130. The connective member 90 is deformed in a fully relaxed random coil. The pressurized drive fluid, which continues to be fed from the pump 46 into the pressurizing chamber 64 via the drive fluid line 58, begins to build up in the pressurizing chamber 64 due to closure of the drive fluid outlet valve 78. The drive fluid buildup causes a drive fluid pressure increase in the head space 134 of the pressurizing chamber 64 which is substantially greater than the treatment fluid back pressure in the treatment pad 12. The drive fluid pressure exerts a substantial downward force on the treatment fluid level 130 in the pressurizing chamber 64 indicated by the directional arrows. The flapper valve 74 is going from the open position to the closed position, indicated by the directional arrow, in response to the increased drive fluid pressure which acts on the stored treatment fluid 40. Upon closure of the flapper valve 74, the check valve 76 goes to the open position in response to the pressure of the stored treatment fluid 40 which is driven into the pad inlet line 22 because it is unable to escape from the pressurizing chamber 64 through the closed flapper valve 74.

FIG. 5D shows the flow control assembly 44 at an intermediate point in the treatment fluid discharging mode of operation. The valve pin 80 remains in the closed position below the valve seat 82 due to the elevated drive fluid pressure in the pressurizing chamber 64 which exceeds the ambient atmospheric pressure external to the pressurizing chamber 64. There is also an absence of any significant downward pulling force on the valve pin 80 from the still partially relaxed connective member 90. With the drive fluid outlet valve 78 closed, the pump 46 continues to deliver pressurized drive fluid to the pressurizing chamber 64 indicated by the directional arrows. As a result, a significant volume of fresh cold treatment fluid 40 is displaced from the pressurizing chamber 64 through the open check valve 76 into the treatment pad 12 indicated by the directional arrows, while the flapper valve 74 is closed. The treatment fluid level 130 in the pressurizing chamber 64 consequently drops, causing a declining buoyant force and a corresponding drop in the displacement member 84.

The fresh cold treatment fluid 40, which is displaced into the treatment pad 12 at a treatment fluid displacement pressure exceeding the resistive back pressure of the treatment pad 12, subsequently displaces the warmer treatment fluid residing in the treatment pad 12. The resistive back pressure is a function of the flow restriction in the pad outlet line 24. The warmer treatment fluid displaced from the treatment pad 12 is returned to the treatment fluid storage vessel 36 via the pad outlet line 24 and discharged into the fresh cold treatment fluid 40 from the distal end 24b as shown by the directional arrow in the pad outlet line 24. The warmer treatment fluid is renewed in the treatment fluid storage vessel 36 by mixing with the fresh cold treatment fluid 40 because the volume of fresh cold treatment fluid 40 is several times greater than the volume of warmer treatment fluid from the treatment pad 12.

Ultimately the falling treatment fluid level 130 in the pressurizing chamber 64 drops the displacement member 84 to the maximum downward level, retransitioning the flow control assembly 44 from the treatment fluid discharging mode shown in FIG. 5D back to the treatment fluid receiving mode shown in FIG. 5A and completing one operational cycle of the flow control assembly 44. The operational cycles are performed continuously and repeatedly for the duration of the desired treatment period. Operation of the flow control assembly 44 is terminated by terminating operation of the pump 46.

Although not shown, it is within the purview of the skilled artisan to construct an alternate embodiment of a flow control assembly employing the present teaching which omits the connective member mechanically linking the displacement member and valve pin. A switch is provided in this embodiment which transitions the drive fluid outlet valve between the open and closed positions in the absence of a mechanical linkage between the displacement member and valve pin. For example, one or more sensors may be positioned in the lower section which are in electrical communication with a valve switch. The switch electromechanically or electronically transitions the drive fluid outlet valve when the sensor indicates that the displacement member has reached its maximum downward or upward level. It is further within the purview of the skilled artisan to construct an alternate embodiment of a flow control assembly employing the present teaching which omits the connective member and the drive fluid outlet valve. A switch is provided in this embodiment which activates or deactivates the pump, respectively, in response to the position of the displacement member. For example, one or more sensors may be positioned in the lower section which are in electrical communication with a pump switch. The switch electromechanically or electronically activates or deactivates the pump when the sensor indicates that the displacement member has reached its maximum downward or upward level.

Figure 6:
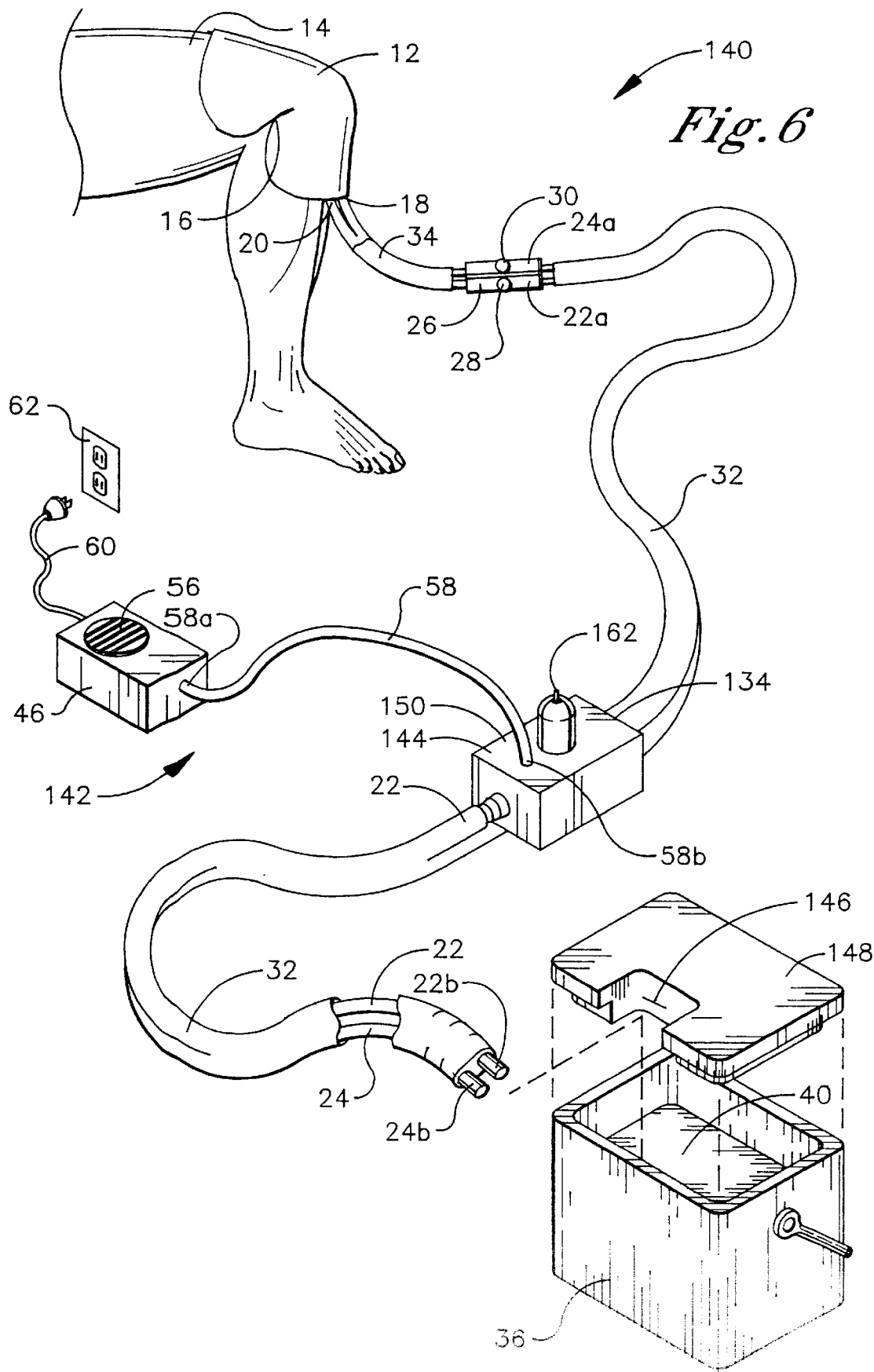
FIG. 6 is a perspective view of a therapeutic treatment system including a partially exploded perspective view of an alternate embodiment of a fluid drive mechanism.
Figure 7:
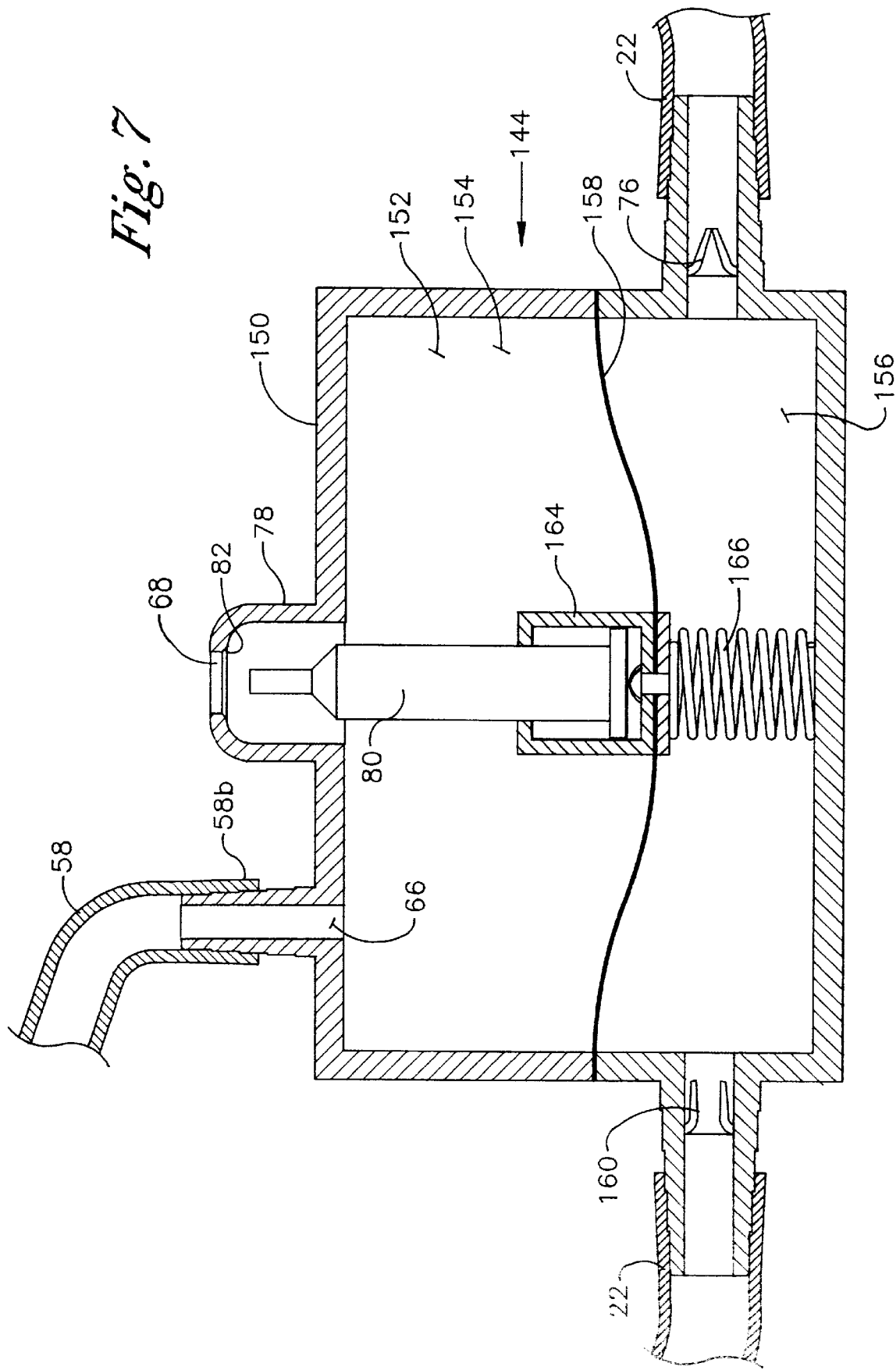
FIG. 7 is a partial cross-sectional view of a flow control assembly included within the fluid drive mechanism of FIG. 6.

An alternate embodiment of a fluid drive mechanism is described below with reference to FIGS. 6 and 7. Referring initially to FIG. 6, a therapeutic treatment system is shown and generally designated 140. The system 140 employs the fluid drive mechanism 142 having a flow control assembly 144 and pump 46. The system 140 is substantially the same as the system 10 with the exception of the fluid drive mechanism 142. The components of FIG. 6 which are substantially identical to those of FIG. 1 are identified in FIG. 6 by the same reference characters as FIG. 1.

The flow control assembly 144 is adapted for in-line mounting intermediately along the length of the pad inlet line 22 remote from the treatment fluid storage vessel 36. The distal ends 22b, 24b of the pad inlet and outlet lines 22, 24, respectively, extend directly into the treatment fluid storage vessel 36 remote from the flow control assembly 144. A slot 146 is provided in the cover 148 of the treatment fluid storage vessel 36 to receive the pad inlet and outlet lines 22, 24 into the treatment fluid storage vessel 36 when the cover 148 is in place.

Details of the flow control assembly 144 are described below with reference to FIG. 7. The components of FIG. 7 which are substantially identical to those of FIG. 2 are identified in FIG. 7 by the same reference characters as FIG. 2. The flow control assembly 144 comprises a housing 150 formed from a durable, waterproof, rigid, hard plastic which encloses a pressurizing chamber 152. The housing 150 defines the sidewalls of the pressurizing chamber 152, which are rigidly configured and have a fixed geometry. The interior of the pressurizing chamber 152 is divided into a drive fluid compartment 154 and a treatment fluid compartment 156 by a displacement member 158. The displacement member 158 is a continuous fluid-impermeable flexible diaphragm, preferably formed from an elastomeric material, which is anchored and sealed along its outer edge to the sidewall of the pressurizing chamber 152. The drive fluid and treatment fluid compartments 154, 156 are in fluid isolation from one another and have variable volumes depending on the position of the displacement member 158.

The flow control assembly 144 is provided with treatment fluid inlet and outlet valves 160, 76 which are one-way check valves. The flow control assembly 144 is also provided with a drive fluid outlet valve 78 comprising a valve pin 80 and a valve seat 82. It is noted that both the fluid inlet and outlet valves 160, 76 are passive valves which only operate in response to pressure changes caused by the action of the drive fluid outlet valve 78, as will be apparent below in describing operation of the flow control assembly 144. The displacement member 158 is centrally anchored to the valve pin 80 by means of a connective member 164 in the form of a rigid bracket which slidably retains the base of the valve pin 80. A biasing member 166 is provided in the form of a coiled spring which is riveted to the connective member 164. The biasing member 166 biases the displacement member 158 upward. It is apparent that the upward force of the biasing member 166 is analogous to the upward force produced by the hydrostatic head of the treatment fluid level 132 in the treatment fluid storage vessel 36 of the therapeutic treatment system 10.

Although not shown, it is apparent to the skilled artisan from the present teaching that the flow control assembly 44 can also be adapted to utilize the above-described displacement member 158. Similarly, the flow control assembly 144 can be adapted to utilize the displacement member 84.

Referring to FIG. 8, an alternate flow control assembly is shown and generally designated 170. The flow control assembly 170 is preferably employed in the therapeutic treatment system 140 of FIG. 6, as an alternative to the flow control assembly 144 shown in FIG. 7. The components of FIG. 8 which are substantially identical to those of FIG. 7 are identified in FIG. 8 by the same reference characters as FIG. 7. The flow control assembly 170 employs a rigid slidable piston as the displacement member 172 of the drive fluid outlet valve 78. The displacement member 172 slidably engages the sidewall of the pressurizing chamber 152, dividing the interior into the drive fluid and treatment fluid compartments 154, 156 which are in fluid isolation from one another. In all other respects, the flow control assemblies 144, 170 are substantially identical, both structurally and operationally.

Figure 9A:
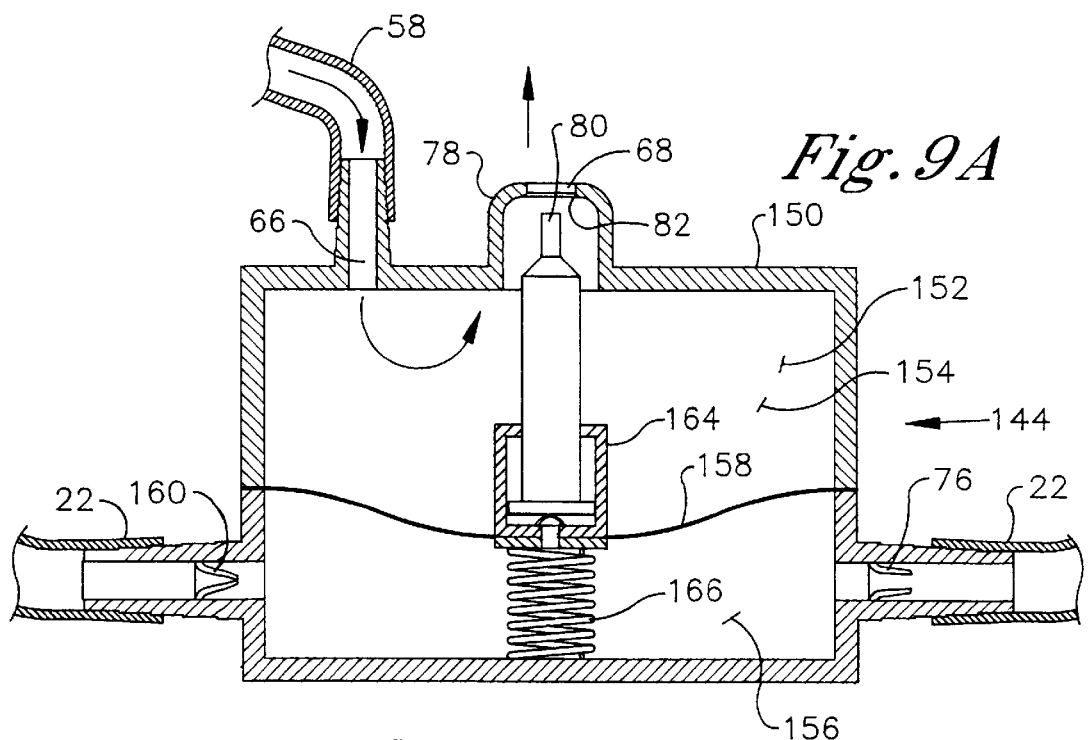
FIGS. 9A–9D are partial cross-sectional views of the flow control assembly of FIG. 7 in a series of operating modes comprising a single operating cycle.

Since operation of the flow control assemblies 144, 170 is substantially similar. a method of operating the flow control assembly 144 is described below with reference to FIGS. 6 and 9A–9D. It is readily within the purview of the skilled artisan, however, to adapt the following operating method to the alternate flow control assembly 170. Operation is initiated by conducting a startup of the system 140 in a substantially similar manner as described above for startup of the system 10. FIG. 9A shows the flow control assembly 144 at the outset of an operating cycle. Specifically, FIG. 9A shows the flow control assembly 144 at the precise time when the assembly 144 has just completed the treatment fluid discharging mode of operation and is transitioning to the treatment fluid receiving mode of operation.

At the outset of the receiving mode of operation, the displacement member 158 has been flexed to a maximum downward level toward the bottom of the pressurizing chamber 152. The valve pin 80 has transitioned to an open position resting against the bottom of the connective member 164. The valve pin 80 has disengaged the valve seat 82 in response to the downward pulling force of the connective member 164 which is greater than the expansion force of the biasing member 166. This transition point occurs when the volume of the treatment fluid compartment 156 is minimized and the displacement member 158 is at the maximum downward level. The pressurized drive fluid is fed by the continuously-operating pump 46 into the drive fluid compartment 154 via the drive fluid line 58. However, the drive fluid compartment 154 remains substantially at ambient atmospheric pressure because the pressurized drive fluid immediately exits the drive fluid compartment 154 via the open drive fluid outlet valve 78 into the surrounding atmosphere indicated by the directional arrows. The free cross-sectional area of the drive fluid outlet port 68 is substantially greater than the free cross-sectional area of the drive fluid inlet port 66 when the drive fluid outlet valve 78 is open, preventing a substantial pressure buildup in the pressurizing chamber 152 during the receiving mode.

The treatment fluid outlet valve 76 is going from the open position to the closed position in response to the treatment fluid back pressure in the treatment pad 12 and the suction force of the displacement member 158. The displacement member 158 is initiating its upward flex in response to the expansion force of the biasing member 166 indicated by the directional arrow. Conversely, the treatment fluid inlet valve 160 is going from the closed to the open position in response to the upward suction force of the displacement member 158.

Figure 9B:
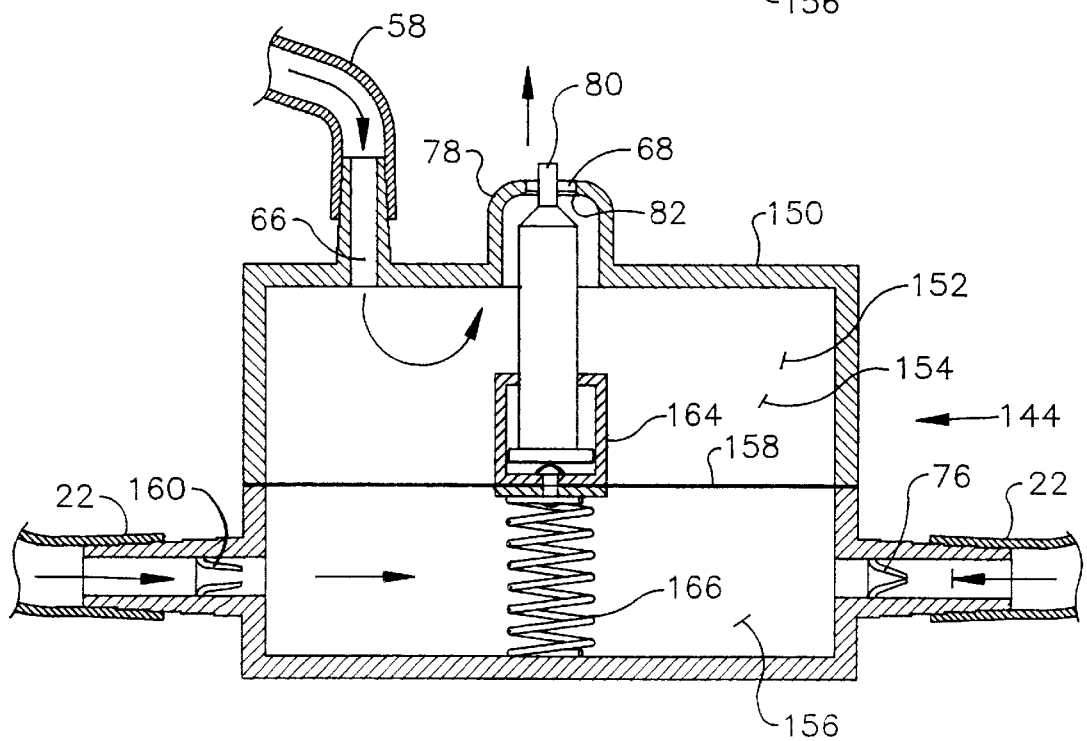

FIG. 9B shows the flow control assembly 144 at an intermediate point in the treatment fluid receiving mode of operation. The suction force of the displacement member 158 caused by the expansion force of the biasing member 166 has opened the treatment fluid inlet valve 160, drawing a significant volume of treatment fluid 40 into the treatment fluid compartment 156 from the treatment fluid storage vessel 36 indicated by the directional arrows. The valve pin 80 stays in the open position below the valve seat 82. Thus, the pressurized drive fluid continues to pass from the drive fluid line 58 through the drive fluid compartment 154 indicated by the directional arrows and the drive fluid compartment 154 remains at ambient atmospheric pressure. The treatment fluid outlet valve 76 in the pad inlet line 22 remains closed in response to the treatment fluid back pressure in the treatment pad 12.

Figure 9C:
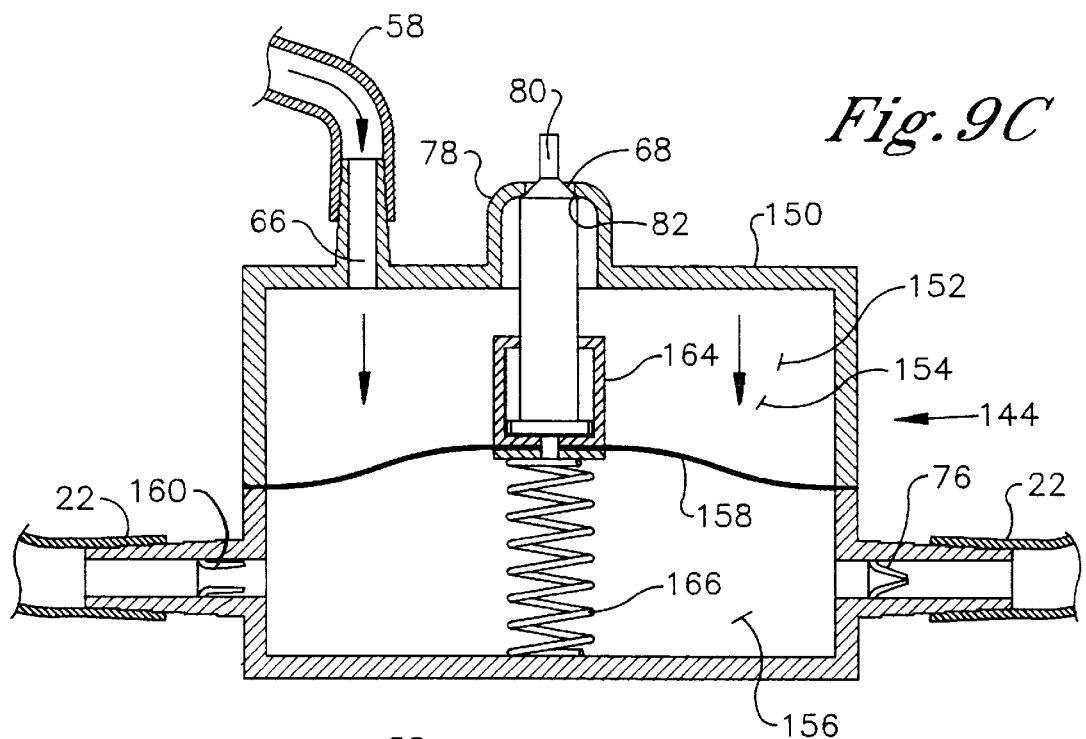

FIG. 9C shows the flow control assembly 144 at the precise time when the flow control assembly 144 has just completed the treatment fluid receiving mode of operation and is transitioning to the treatment fluid discharging mode of operation. At the outset of the discharging mode of operation, the displacement member 158 has been flexed to a maximum upward level toward the top of the pressurizing chamber 152. The valve pin 80 has transitioned to a closed position in the valve seat 82 in response to the upward force of the bottom of the connective member 164 abutting the valve pin 80 which results from the expansion force of the biasing member 166. This transition point occurs when the volume of the treatment fluid compartment 156 is maximized and the displacement member 158 is positioned at the maximum upward level. The pressurized drive fluid, which continues to be fed from the pump 46 into the drive fluid compartment 154 via the drive fluid line 58, begins to build up in the drive fluid compartment 154 due to closure of the drive fluid outlet valve 78. The drive fluid buildup causes a drive fluid pressure increase in the drive fluid compartment 154 which is substantially greater than the treatment fluid back pressure in the pad 12 and the expansion force of the biasing member 166. The drive fluid pressure exerts a substantial downward force on the displacement member 158 indicated by the directional arrows. The drive fluid pressure initiates a downward flex in the displacement member 158. The treatment fluid outlet valve 76 is going from the closed position to the open position in response to the drive fluid pressure increase which acts on the stored treatment fluid 40. The treatment fluid inlet valve 160 is going from the open position to the closed position in response to the back pressure in the treatment fluid compartment 156.

Figure 9D:
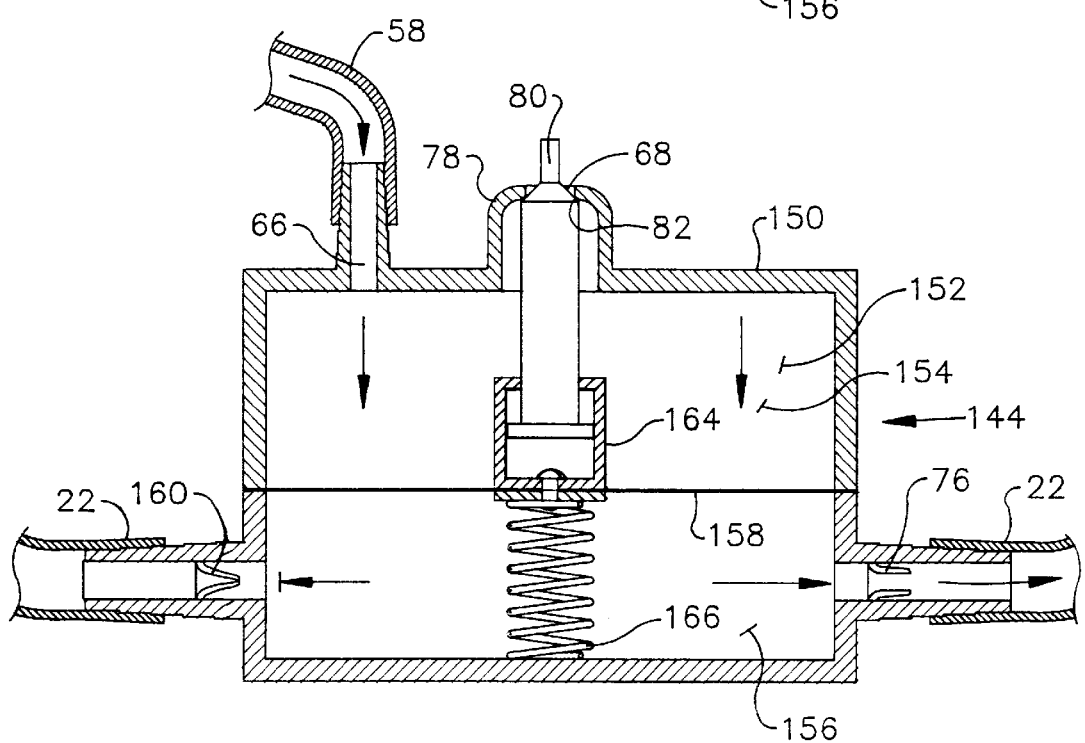

FIG. 9D shows the flow control assembly 144 at an intermediate point in the treatment fluid discharging mode of operation. The valve pin 80 remains in the closed position below the valve seat 82 due to the elevated drive fluid pressure in the drive fluid compartment 154 which exceeds the ambient atmospheric pressure external to the drive fluid compartment 154. There is also an absence of any significant downward pulling force on the valve pin 80. With the drive fluid outlet valve 78 closed, the pump 46 continues to deliver pressurized drive fluid to the drive fluid compartment 154 indicated by the directional arrows. As a result, a significant volume of fresh cold treatment fluid 40 is displaced from the treatment fluid compartment 156 through the open treatment fluid outlet valve 76 into the treatment pad 12 indicated by the directional arrows.

The fresh cold treatment fluid 40, which is displaced into the treatment pad 12 at a treatment fluid displacement pressure exceeding the resistive back pressure of the treatment pad 12, subsequently displaces the warmer treatment fluid residing in the treatment pad 12. The warmer treatment fluid displaced from the treatment pad 12 is returned to the treatment fluid storage vessel 36 via the pad outlet line 24 and discharged into the fresh cold treatment fluid 40 from the distal end 24b. Ultimately the displacement member 158 flexes to the maximum downward level, retransitioning the flow control assembly 144 from the treatment fluid discharging mode shown in FIG. 9D back to the treatment fluid receiving mode shown in FIG. 9A and completing one operational cycle of the flow control assembly 144. The operational cycles are performed continuously and repeatedly for the duration of the desired treatment period. Operation of the flow control assembly 144 is terminated by disconnecting the pump 46 from the power source.

While the foregoing preferred embodiments of the invention have been described and shown, it is understood that all alternatives and modifications, such as those suggested and others, may be made thereto and fall within the scope of the invention.

We claim:

1. A drive mechanism for a therapeutic treatment system comprising:

a treatment fluid storage vessel;

a drive fluid pump;

a pressurizing chamber for conveying a stored treatment fluid, said pressurizing chamber having a drive fluid inlet for receiving a pressurized drive fluid from said drive fluid pump, a treatment fluid inlet for receiving said stored treatment fluid from said treatment fluid storage vessel, a treatment fluid outlet for discharging said stored treatment fluid, and a drive fluid outlet for discharging said drive fluid; and a drive fluid outlet valve having an open position and a closed position to selectively control discharge of said drive fluid from said pressurizing chamber via said drive fluid outlet, wherein said drive fluid outlet valve automatically transitions to said open position to discharge said drive fluid via said drive fluid outlet in response to a substantial volume decrease of said stored treatment fluid in said pressurizing chamber and automatically transitions to said closed position to block discharge of said drive fluid via said drive fluid outlet in response to a substantial volume increase of said stored treatment fluid in said pressurizing chamber.

2. The drive mechanism of claim 1 further comprising a treatment fluid inlet valve having an open position and a closed position to substantially inhibit back flow of said stored treatment fluid from said pressurizing chamber to said treatment fluid storage vessel, wherein said treatment fluid inlet valve automatically transitions to said closed position to block discharge of said treatment fluid from said pressurizing chamber via said treatment fluid inlet and divert discharge of said treatment fluid from said pressurizing chamber via said treatment fluid outlet in response to a substantial volume increase of said stored treatment fluid in said pressurizing chamber and automatically transitions to said open position to permit entry of said treatment fluid into said pressurizing chamber via said treatment fluid inlet in response to a substantial volume decrease of said stored treatment fluid in said pressurizing chamber.

3. The drive mechanism of claim 1 further comprising a displacement member displaceable between a first position and a second position within said pressurizing chamber to transition said drive outlet valve between said open position and said closed position.

4. The drive mechanism of claim 3 wherein said displacement member is buoyantly displaceable by said stored treatment fluid.

5. The drive mechanism of claim 3 wherein said displacement member is a slidable piston.

6. The drive mechanism of claim 3 wherein said displacement member is a flexible diaphragm.

7. The drive mechanism of claim 1 wherein said treatment fluid outlet is in substantial fluid isolation from said drive fluid.

8. The drive mechanism of claim 1 wherein said treatment fluid inlet is in substantial fluid isolation from said drive fluid.

9. A device for therapeutically treating a desired portion of the body of a patient with a nonambient temperature treatment fluid comprising:
 a treatment fluid storage vessel retaining a nonambient temperature stored treatment fluid;
 a pad positionable on the desired portion of the body, said pad having pad inlet, a pad outlet, and a continuous pad flowpath from said pad inlet to said pad outlet;
 a pad inlet line connected to said pad inlet;
 a pad outlet line connected to said pad outlet for discharging treatment fluid from said pad;
 a drive fluid pump; and
 a pressurizing chamber for circulating said stored treatment fluid from said treatment fluid storage vessel through said pad flowpath, said pressurizing chamber having a drive fluid inlet for receiving a pressurized drive fluid from said drive fluid pump, a treatment fluid inlet for receiving said stored treatment fluid from said treatment fluid storage vessel, and a treatment fluid outlet connected to said pad inlet line for discharging said stored treatment fluid into said pad inlet line under the force of said pressurized drive fluid when a substantial volume increase of said stored treatment fluid occurs in said pressurizing chamber, wherein said treatment fluid outlet is in substantial fluid isolation from said drive fluid.

10. The device of claim 9 wherein said pressurizing chamber has a drive fluid outlet for discharging said drive fluid to said ambient atmosphere.

11. The device of claim 10 further comprising a drive fluid outlet valve having an open position and a closed position to selectively control discharge of said drive fluid from said pressurizing chamber via said drive fluid outlet, wherein said drive fluid outlet valve automatically transitions to said open position to discharge said drive fluid via said drive fluid outlet in response to a substantial volume decrease of said stored treatment fluid in said pressurizing chamber and automatically transitions to said closed position to block discharge of said drive fluid via said drive fluid outlet in response to a substantial volume increase of said stored treatment fluid in said pressurizing chamber.

12. The drive mechanism of claim 11 further comprising a displacement member displaceable between a first position and a second position within said pressurizing chamber to transition said drive outlet valve between said open position and said closed position.

13. The drive mechanism of claim 12 wherein said displacement member is buoyantly displaceable by said stored treatment fluid.

14. The drive mechanism of claim 12 wherein said displacement member is a slidable piston.

15. The drive mechanism of claim 12 wherein said displacement member is a flexible diaphragm.

16. The drive mechanism of claim 9 further comprising a treatment fluid inlet valve having an open position and a closed position to substantially inhibit back flow of said stored treatment fluid from said pressurizing chamber to said treatment fluid storage vessel, wherein said treatment fluid inlet valve automatically transitions to said closed position to block discharge of said treatment fluid from said pressurizing chamber via said treatment fluid inlet and divert discharge of said treatment fluid from said pressurizing chamber via said treatment fluid outlet in response to a substantial volume increase of said stored treatment fluid in said pressurizing chamber and automatically transitions to said open position to permit entry of said treatment fluid into said pressurizing chamber via said treatment fluid inlet in response to a substantial volume decrease of said stored treatment fluid in said pressurizing chamber.

17. A drive mechanism for a therapeutic treatment system comprising:
 means for storing a stored treatment fluid;
 means for pressurizing a drive fluid;
 means for receiving said pressurized drive fluid and said stored treatment fluid and enabling a substantial volume buildup of said stored treatment fluid in said receiving means over time;
 means for selectively discharging said volume buildup of said stored treatment fluid from said receiving means to a therapeutic treatment site under the force of said pressurized drive fluid in response to said volume buildup in said receiving means; and
 means for discharging said pressurized drive fluid from said receiving means during said volume buildup and retaining said pressurized drive fluid in said receiving means upon completion of said volume buildup in said receiving means.

18. A method for driving a nonambient temperature treatment fluid through a therapeutic treatment system:
 storing a nonambient temperature stored treatment fluid in a vessel;
 feeding said stored treatment fluid to a pressurizing chamber in fluid communication with said vessel during a receiving mode of operation for a sufficient period of time to cause a substantial volume increase of said stored treatment fluid in said pressurizing chamber; and
 transitioning to a discharging mode of operation when said volume increase is achieved by interrupting said feeding of said stored treatment fluid to said pressurizing chamber from said vessel and accumulating a pressurized drive fluid in said pressurizing chamber for a sufficient period of time to cause a substantial pressure increase in said pressurizing chamber, wherein said pressure increase drives said volume increase of said stored treatment fluid from said pressurizing chamber.

19. The method of claim 18 further comprising transitioning to said receiving mode of operation when said volume increase of said stored treatment fluid is driven from said pressurizing chamber and thereafter continuously and sequentially repeating said receiving and said discharging modes of operation.

20. A drive mechanism for a therapeutic treatment system comprising:
 a treatment fluid storage vessel;

a drive fluid pump;

a pressurizing chamber for conveying a stored treatment fluid, said pressurizing chamber having a drive fluid inlet for receiving a pressurized drive fluid from said drive fluid pump, a treatment fluid inlet for receiving said stored treatment fluid from said treatment fluid storage vessel, a treatment fluid outlet for discharging said stored treatment fluid and a drive fluid outlet for discharging said drive fluid;

a drive fluid outlet valve having an open position and a closed position to selectively control discharge of said drive fluid from said pressurizing chamber via said drive fluid outlet; and an interface having a variable position in said pressurizing chamber between said stored treatment fluid and said drive fluid, wherein said treatment fluid inlet and outlet are on a first side of said interface and said drive fluid inlet and outlet are on an opposite second side of said interface and wherein said position of said interface approaches said first side when said drive fluid inlet valve is closed and approaches said second side when said drive fluid inlet valve is open.

21. The drive mechanism of claim 20 wherein said interface is a fluid contact surface of said drive fluid and said stored treatment fluid.

22. The drive mechanism of claim 20 wherein said interface is a slidable piston contacted by said stored treatment fluid on said first side and contacted by said drive fluid on said second side.

23. The drive mechanism of claim 20 wherein said interface is a flexible diaphragm contacted by said stored treatment fluid on said first side and contacted by said drive fluid on said second side.

24. The drive mechanism of claim 20 wherein said treatment fluid outlet is in substantial fluid isolation from said drive fluid.

25. The drive mechanism of claim 20 wherein said treatment fluid inlet is in substantial fluid isolation from said drive fluid.

* * * * *